(12) United States Patent
Williams

(10) Patent No.: US 9,445,933 B2
(45) Date of Patent: Sep. 20, 2016

(54) VACUUM SPLINT

(75) Inventor: Gary R. Williams, Carlsbad, CA (US)

(73) Assignee: HARTWELL MEDICAL LLC, Carlsbad, CA (US)

( * ) Notice: Subject to any disclaimer, the term of this patent is extended or adjusted under 35 U.S.C. 154(b) by 379 days.

(21) Appl. No.: 13/251,801

(22) Filed: Oct. 3, 2011

(65) Prior Publication Data

US 2012/0277644 A1    Nov. 1, 2012

Related U.S. Application Data

(60) Provisional application No. 61/388,824, filed on Oct. 1, 2010.

(51) Int. Cl.
*A61F 5/058* (2006.01)

(52) U.S. Cl.
CPC ................... *A61F 5/05833* (2013.01)

(58) Field of Classification Search
USPC ...... 602/5, 6, 13, 19, 20; 128/845, 846, 847, 128/869, 870, 873, 874; 5/632, 630, 621, 5/623, 624, 625, 626, 628, 701–702
See application file for complete search history.

(56) References Cited

U.S. PATENT DOCUMENTS

| | | |
|---|---|---|
| 3,745,998 A | 7/1973 | Rose |
| 4,045,830 A * | 9/1977 | Loeb et al. ................. 5/81.1 T |
| 4,157,713 A | 6/1979 | Clarey |
| 4,657,003 A | 4/1987 | Wirtz |
| 5,074,288 A * | 12/1991 | Miller ............................ 602/19 |
| 5,121,756 A * | 6/1992 | Koledin ........................... 5/628 |
| 5,626,150 A * | 5/1997 | Johnson et al. .................. 5/628 |
| 5,722,729 A * | 3/1998 | Carilli ...................... 297/452.55 |
| 6,308,353 B1 * | 10/2001 | Van Steenburg ................ 5/632 |
| 8,240,310 B2 * | 8/2012 | Soung .......................... 128/845 |
| 8,469,911 B2 * | 6/2013 | Hiebert .......................... 602/13 |

OTHER PUBLICATIONS

Emergency Medical Product Catalog, BoundTree Medical, catalog, 2010-2011, pp. 182-185.
Catalog No. 920, Life-Assist, Inc., catalog, 2008-2009, pp. 65-66.

* cited by examiner

*Primary Examiner* — Ophelia A Hawthorne
(74) *Attorney, Agent, or Firm* — Todd J. Langford; Eric A. Hanscom

(57) ABSTRACT

A vacuum splint for maintaining a person in an immobilized state includes a flexible airtight casing upon which a patient is placed. The casing has an internal chamber that contains a large number of beads. Valves are provided to develop a vacuum within the chamber to convert the casing from a relatively soft, flexible state to a rigid, evacuated state. A semi-rigid member spans the length of the vacuum splint that resists longitudinal compression when air is evacuated from the chamber. The semi-rigid member also retains sufficient longitudinal and lateral flexibility such that it allows the vacuum splint to be molded to various patient positions and folded or rolled up when not in an evacuated state. The head end of the vacuum splint includes two protrusions that extend upward. When in an evacuated state, these protrusions extend over either side of a patient's head thereby providing support and protection.

20 Claims, 3 Drawing Sheets

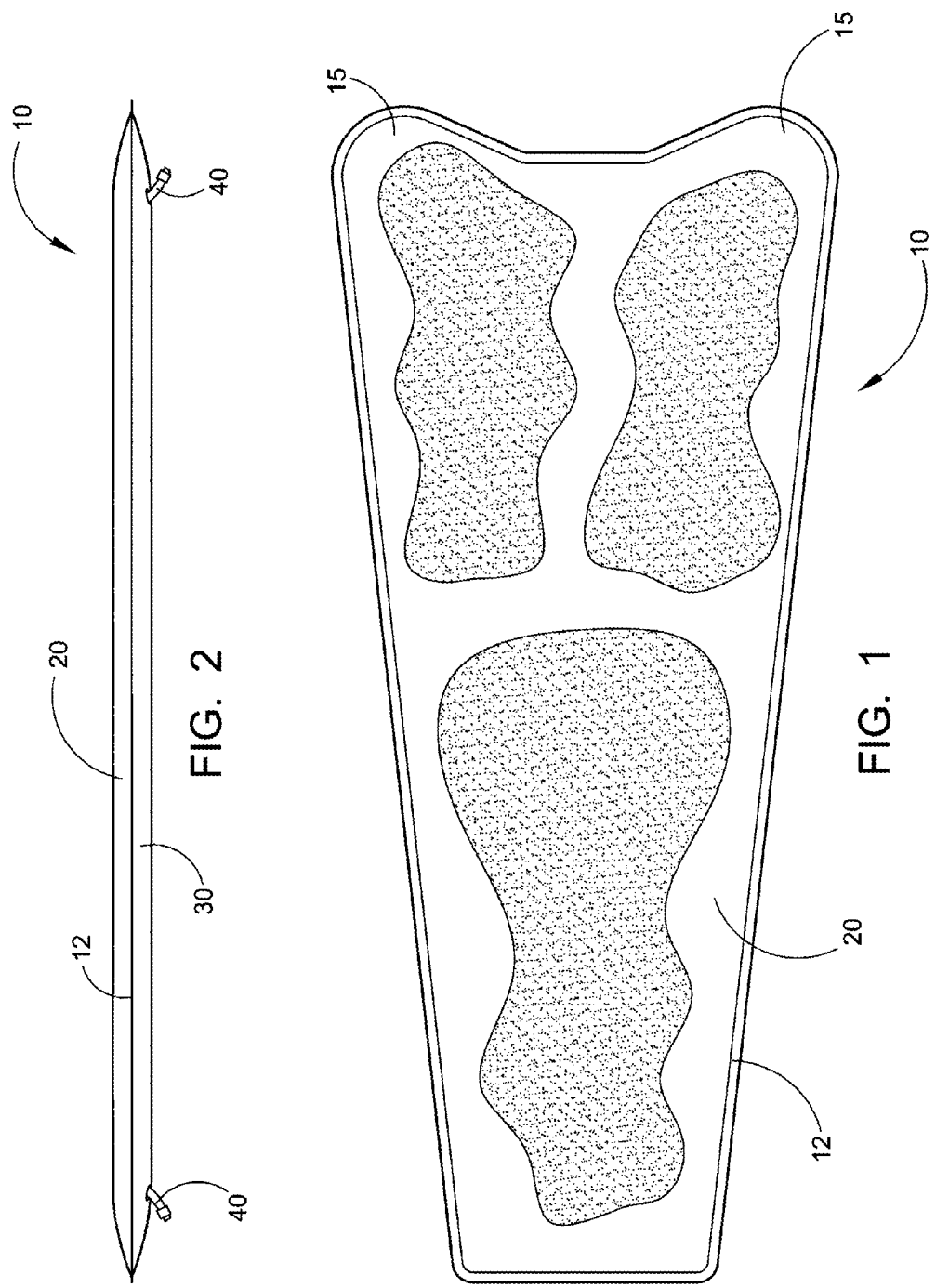

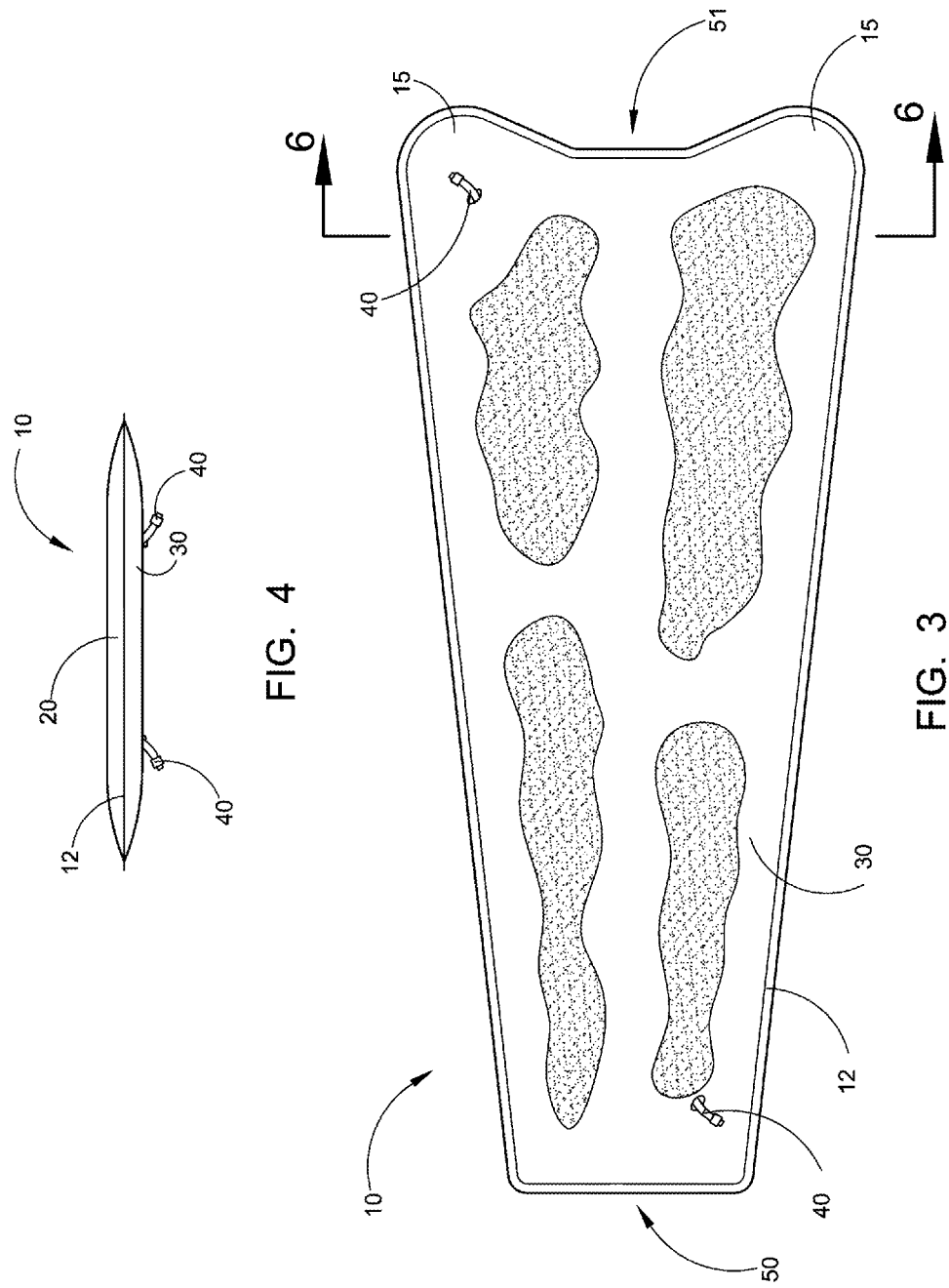

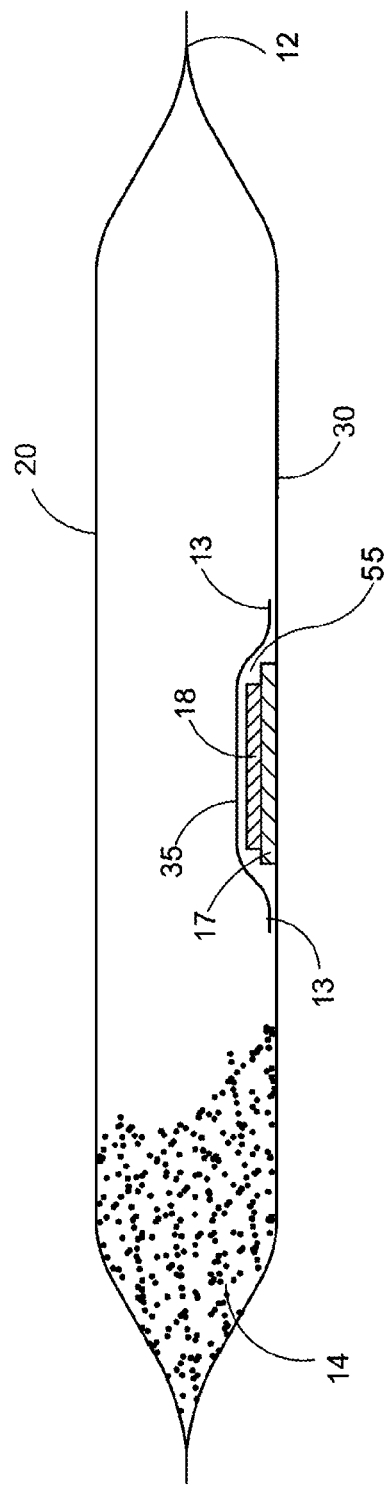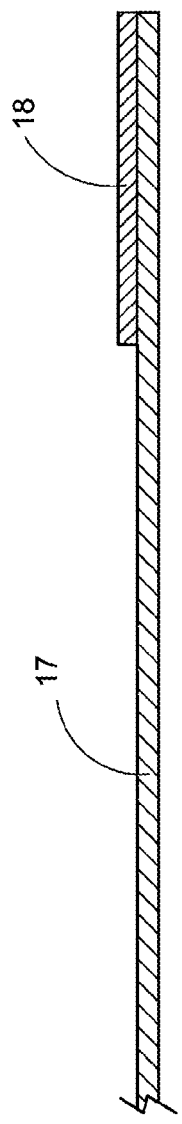
FIG. 6
FIG. 5

VACUUM SPLINT

CROSS REFERENCE TO RELATED APPLICATIONS

This application is a non-provisional application of U.S. Provisional Patent Application No. 61/388,824 filed on Oct. 1, 2010, the entirety of which is hereby incorporated by reference.

STATEMENT REGARDING FEDERALLY SPONSORED RESEARCH OR DEVELOPMENT

This invention was not federally sponsored.

BACKGROUND OF THE INVENTION

Field of the Invention

This invention relates to the general field of medical splints, and more specifically toward a vacuum splint for maintaining a person in an immobilized state. The vacuum splint includes a flexible airtight casing upon which a patient may be placed. The casing has an internal chamber that contains a large number of beads. One or more means of air evacuation are provided to develop a vacuum within the chamber to convert the casing from a relatively flexible state to a rigid, evacuated state. A semi-rigid member spans the length of the vacuum splint. This semi-rigid member resists longitudinal compression when air is evacuated from the chamber. At the same time, the semi-rigid member is flexible such that it allows the vacuum splint to fold or roll up when the vacuum splint is not in an evacuated state. The head end of the vacuum splint includes two protrusions on either side that extend upward. When in an evacuated state, these protrusions extend over either side of a patient's head thereby providing support and protection.

Transportation of accident victims in an immobilized state is widely recognized as important to prevent secondary trauma. Immobilizing other classes of patients is beneficial as well.

In-hospital transportation of patients from their rooms to other areas of the hospital for special diagnostic procedures or for special treatment involves a number of changes in patient position, any one of which could aggravate existing medical afflictions. The patient must be lifted and transferred from bed to gurney or wheelchair, transported to the desired area, and in like manner must be physically moved about for diagnosis or treatment, etc. and then returned to his or her room. Where immobilization is critically important, as in spinal injury cases, the patient is typically strapped down firmly onto a backboard, which is then placed on the gurney. Even this does not always prevent secondary trauma from occurring because of lateral forces acting on the patient during turning of the gurney or tipping of the backboard, for example.

Trauma also develops because the weight of the patient is unevenly distributed over the hard backboard. The prominent bones of the body rest upon the board, developing pressure points, while the body structure between these pressure points is relatively unsupported. Bedridden patients also suffer from the effects of these pressure points over a long period of time.

What has just been said about the desirability of better immobilization of patients lying or transported in a prostrate position also applies to patients in wheelchairs. In fact, it is sometimes even more difficult to avoid aggravation of preexisting injuries when moving patients into and out of wheelchairs, or into and out of vehicles.

Recent studies have suggested the importance of proper patient immobilization following an accident. Fully twenty percent of paraplegia has been attributed to improper handling of victims following the accidents.

The victims of Marfan Syndrome are a tragic example of the need for adequate patient immobilization. This genetic disease affects the connective tissue of the skeleton, lungs, eyes, heart and other organ systems such that the tissue does not hold the body parts in proper position. When the joints cannot be held in position the body will not support its own weight and the patient becomes bedridden. Attempts to transport such patients have resulted in dislocated joints, followed by days of pain and severe swelling until the joints have returned to their normal positions. This has occurred even when the patient has been transported within a protective cast resting upon layers of cushioning material.

One of the better immobilization means of the prior art is a vacuum or air evacuated bag or casing, which is filled with small discrete elements such as round beads. The bag completely underlies the patient and is made wide enough to come up along the sides of the patient for cradling and supporting the body. When air is evacuated from the bag, it becomes rigid and immobilizes the patient in a protective cocoon.

U.S. Pat. No. 5,121,756 to Koledin teaches a vacuum immobilizer support with stiffener means that comprises transversely spaced apart slats or narrow boards or battens disposed in two sets of pockets which are longitudinally spaced apart and extend longitudinally through the neck and thoracic regions, and through the pelvic region, respectively. These battens prevent any transverse bending or pivotal movement of the casing in these regions in the rigidified state of the casing. However, their transverse spacing permits the casing to be wrapped or pivoted about longitudinal axes to conform the unevacuated casing to the contours of the patient.

SUMMARY OF THE INVENTION

The current invention provides a vacuum splint for maintaining a person in an immobilized state. The vacuum splint includes a flexible airtight casing upon which a patient may be placed. The casing contains a large number of discrete elements, such as beads, therein. One or more means of air evacuation are used to develop a vacuum within the casing to convert the casing from a relatively soft, flexible state to a rigid, evacuated state. A semi-rigid member spans the length of the vacuum splint. This semi-rigid member resists longitudinal compression, especially when air is being evacuated. At the same time, the semi-rigid member retains sufficient longitudinal and laterally flexibility such that it allows the vacuum splint to fold or roll up when not in an evacuated state. The head end of the vacuum splint includes two protrusions, one on each side that extends upward. When in an evacuated state, these protrusions extend over either side of a patient's head thereby providing support and protection.

It is a principal object of the invention to provide a vacuum splint for immobilizing a patient that produces few if any pressure points on the patient.

It is another object of the invention to provide a vacuum splint for immobilizing a patient that properly stabilizes the patient's head.

It is a final object of this invention to provide a vacuum splint that can be rolled or otherwise be compacted for easy transport and storage.

As used herein, a vacuum is intended to be a space from which air has been completely or partly removed.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE FIGURES

The accompanying drawings, which are incorporated in and form a part of this specification, illustrate embodiments of the invention and together with the description, serve to explain the principles of this invention.

FIG. 1 is a top view of a vacuum splint according to selected embodiments of the current disclosure.

FIG. 2 is a side view of the vacuum splint.

FIG. 3 is a bottom view of the vacuum splint.

FIG. 4 is a head end view of the vacuum splint.

FIG. 5 is a partial side view of the semi-rigid member.

FIG. 6 is a cross-sectional view of the vacuum splint.

DETAILED DESCRIPTION OF THE INVENTION

Many aspects of the invention can be better understood with the references made to the drawings below. The components in the drawings are not necessarily drawn to scale. Instead, emphasis is placed upon clearly illustrating the components of the present invention. Moreover, like reference numerals designate corresponding parts through the several views in the drawings.

FIG. 1 is a top view of a vacuum splint according to the current invention. The vacuum splint 10 has a generally trapezoidal shape. It includes two protrusions 15, or wings, extending out from the head end on both sides of the vacuum splint.

FIG. 2 is a side view of the vacuum splint. Two layers of material are fused together to form a casing and a chamber therein. A seam 12 is created where the top layer of material 20 and the bottom layer of material 30 meet. The chamber has a multitude of beads therein (shown in more detail in FIG. 6). Air is removed from within the chamber and reintroduced into the chamber by means of one or more valves 40. In this figure, two valves are shown, though it must be appreciated by one skilled in the art that as few as one or more than two valves are nonetheless possible and in certain circumstances desirable.

FIG. 3 is a bottom view of the vacuum splint. Two valves 40 are shown attached to the bottom layer of material 30. Having a valve 40 at each end of the vacuum splint 10 provides easy access to the chamber therein. For example, when wrapping the vacuum splint around a patient's head, air can be removed from the foot end 50 of the vacuum splint to avoid unnecessary movement at the head end 51 of the vacuum splint. Alternatively, when the patient is in the hospital, suction is often available towards the head of the patient, whereby an access point located at the head end of the vacuum splint is more convenient.

FIG. 4 is a head end view of the vacuum splint. In a particular embodiment, the valves 40 are located on either side of the vacuum splint, such that there is fluid access to the chamber therein from either the left or right side of the vacuum splint.

A semi-rigid member spanning the length of the vacuum splint is secured to the bottom layer of material. In a particular embodiment, an additional layer of material is fused to the bottom layer of material to retain the semi-rigid member therein. The fusion of the additional layer of material results in seams that travel the length of the vacuum splint and meet the seam traveling around the outer edge of the vacuum splint. However, since the semi-rigid member and additional layer of material are located on the inside part of the bottom layer of material, these parts are not readily visible in FIG. 3 or 4.

FIG. 5 is a partial side view of the semi-rigid member. In a particular embodiment, the semi-rigid member 17 is seventy-two inches long and three and one-half inches wide. At each end of the semi-rigid member 17, there is a rigid support 18 that is eight inches long and three and one-quarter inches wide. The rigid support 18 resists the flexing and curling of the semi-rigid member as a vacuum is created within the chamber.

As air is removed from the vacuum splint, the two layers of material are drawn in, thereby causing compressive forces along the length of the vacuum splint. The semi-rigid member, which spans the length of the vacuum splint from the head end to the foot end, resists these compressive forces. The ends of the vacuum splint also have a tendency to bend or curl when air is evacuated from the chamber. The semi-rigid member, because of its flexibility, does not resist this curling tendency. However, the rigid supports do. By affixing a rigid support to each end of the semi-rigid member, the curling at the ends of the vacuum splint when air is evacuated from the chamber is greatly reduced if not entirely eliminated. The rigid support is longitudinally and laterally rigid and thus restricts lateral movement of the vacuum splint at the ends. At the same time, when the vacuum splint is in a soft state, it may nonetheless be rolled and or folded since the rigid supports are only located at each end of the vacuum splint.

FIG. 6 is a cross-sectional view of the vacuum splint. The cross sectional view of this figure is taken along line 6 shown in FIG. 3. A rigid support 18 is affixed to the semi-rigid member. The semi-rigid member 17, or stiffener, and rigid support 18 are encased between an additional layer of material 35 and the bottom layer of material 30, where these two layers of material are fused together to form a sleeve 55. The meeting of these two layers forms seams 13. The additional layer of material 35, semi-rigid member 17, and rigid support 18 are located on the inside part of the bottom layer of material and thus reside within the chamber. Beads 14 fill the chamber between the top layer of material 20 and bottom layer of material 30.

The top and bottom layers of material are made from a malleable air holding material. In a particular embodiment, the top and bottom layers of material are vinyl/polyester laminates. In another particular embodiment, the bottom layer is a laminated vinyl material. In fact, the bottom layer can have a scrim structure between two layers of vinyl to create the laminated vinyl material. This laminated vinyl material is a stronger material that aids in transporting patients using the vacuum splint. Furthermore, the top layer of material is a non-supported vinyl material. This creates a lighter, more malleable top layer that molds to the specific contours of the patient better than a stiffer, stronger material.

Thus, the vacuum splint may use a stiffer, stronger bottom layer of material and a lighter, more malleable top layer of material to provide a vacuum splint that has sufficient supporting structure while at the same time is easily moldable to the contours of the patient. In another particular embodiment, the top and bottom layers of material are made from materials such as coated vinyls or urethane fabrics. The protrusions are formed from the two layers (top and bottom) of material.

The layers of material are fused together along their edges using means well known in the art, such as radio frequency (RF) welding. However, any such means of fusing the layers together must create a sufficient seal to prevent air from entering between the two layers when air is evacuated from within the chamber.

Beads fill the chamber between the top and bottom layers of material. The beads are preferably polystyrene beads that are treated for fire resistance.

The one or more valves used on the vacuum splint allow air to be evacuated from the vacuum splint and prevent air from entering back into the vacuum splint, until the valve is open or released. The valve preferably mates with a pump that can be used to evacuate the air from within the chamber of the vacuum splint. A quick connect and disconnect system between the valve and pump is preferred, with an audible click to notify a user when the valve and pump are properly mated together. The valves are made from a plastic material, such that they will not interfere with any X-ray or magnetic resonance imaging (MRI) scans that are performed while a patient is secured to the vacuum splint.

In a particular embodiment, the semi-rigid member is made from polyethylene. This material provides sufficient longitudinal support to resist vertical compression of the vacuum splint while at the same time allowing the vacuum splint to be folded or rolled up. The rigid support is made from a relatively stiff material, such as plywood. This material provides sufficient rigidity at the ends of the vacuum splint while not interfering with X-ray or MRI scans.

When air is evacuated from the chamber, the vacuum splint stiffens, but also has a tendency to shrink and thus compress longitudinally, where the head end and foot end move toward each other, unless otherwise restricted. Longitudinal movement of the vacuum splint is not desired, as this could cause unwanted injury to patients with spinal injuries or other injuries that are aggravated by vertical compression. To counteract this effect, a stiffening member is required to resist the movement of the head end of the vacuum splint towards the foot end of the vacuum splint.

The semi-rigid member of the current invention provides the necessary longitudinal rigidity to resist the longitudinal compression of the vacuum splint when air is evacuated from the chamber. The rigid supports resist the tendency of the vacuum splint to curl at each end when in a hardened state (when air is evacuated from the chamber forming a vacuum therein). However, the semi-rigid member can bend, thereby allowing the vacuum splint, when in a softened state, to fold or roll up. For example, the vacuum splint of the current invention can be folded in half, thirds, or quarters as desired. Alternatively, the vacuum splint may be rolled up, whereby the foot end of the vacuum splint can be rolled towards the head end of the vacuum splint to form a spiral shape. These different configurations allow medical personal to configure the vacuum splint in a variety of shapes and sizes for transport and storage. The semi-rigid member also allows for the splint to support patients in a variety of configurations. For example, the splint could be conformed to and support a patient whose knees are flexed. Another example includes conforming the splint to a patient who has kyphosis, or hunchback, whereby the patient's unique curvature of the upper back is supported.

The vacuum splint molds to the contours of the patient's specific injuries. The sealed chamber contains thousands of beads with a small amount of air. When air is removed from this chamber, the beads compact gently against each other forming a rigid mold that serves as an excellent splint platform. The vacuum splint conforms to the exact shape of the injury site without applying unnecessary circumferential pressure. This eliminates the potential for tissue, vessel, and nerve damage, the development of compartment syndrome, unnecessary pressure sores or impaired circulation to the injured area. Additionally, the polystyrene beads act as an excellent thermal insulator, helping to maintain the patient's body temperature and reduce heat loss. Because of the materials used to manufacture the vacuum splint, it will not interfere with X-ray or MRI scans.

The head end of the vacuum splint has a unique shape that includes two protrusions that are like the top half of an angel's wings. This specific shape enables a patient's head to be properly stabilized once the vacuum splint is formed around the patient's head and the air is evacuated from the chamber. Due to the narrower profile of the vacuum splint and the need to mold the splint sufficiently next to the patient's shoulders and both sides of the patient's head, more splint material is needed. The additional splint material is required in order to provide sufficient support along the entire side of the patient's head. Without the two protrusions, a triangular shaped gap is created near the top of the patient's head on both sides, and the patient's head would not be adequately protected and stabilized using the vacuum splint. These protrusions become side support pillows with a vertical end orientation at the head end of the vacuum splint. This design also allows for a narrower overall profile of the vacuum splint while still providing the necessary protection and support to the patient. The reduced size means the vacuum splint is less expensive to produce and transport as well as easier to handle, all of which are extremely important characteristics to emergency medical personnel.

To use the vacuum splint, a patient is placed upon the top side of the vacuum splint before air is evacuated from the chamber. The vacuum splint is then formed to and around the patient's body as necessitated by the circumstances of the patient's situation. Once the vacuum splint is properly conformed to the patient, air is evacuated from the chamber. Air is withdrawn through the one or more valves by means of a pump thereby causing the vacuum splint to stiffen. The pump may be electric or manually operated. Additional means of securing the patient to the vacuum splint may be used and in many cases are preferred, such as using straps. Further, the vacuum splint and patient may be secured to any number of supporting devices such as a backboard, scoop stretcher, CombiCarrier® litter or flat stretcher to provide additional stability and ease of handling by emergency professionals. Once the patient is properly restrained within the vacuum splint, the patient may be transported.

To remove the patient from the vacuum splint, the above steps are performed in reverse. The valve is opened to allow air to enter the chamber, thereby causing the vacuum splint to soften and become flexible. After the patient is removed form the vacuum splint, the splint may be rolled or folded into a variety of configurations for storage or transportation.

In a particular embodiment of the current disclosure, the vacuum splint is manufactured by first cutting the layers of material and silk-screening those layers, if desired. One or more holes are cut into the bottom layer of material and one or more valves are secured thereto, such as by RF welding. The additional layer of material is also welded onto the bottom layer of material thereby creating a sleeve. Next, the top layer of material is RF welded to the bottom layer of material along their edges, except for an area at the bottom end of each layer, forming a chamber between the two layers. Separately, a rigid support is secured to each end of the semi-rigid member by means of an adhesive. The semi-rigid member is then slid into the sleeve between the bottom layer of material and the additional layer of material. Beads are also placed into the chamber between the top layer and bottom layer. The bottom end (or foot end) is then RF welded closed, wherein the sleeve and chambers are sealed closed by welding the bottom layer, additional layer, and top layer together. Finally, air is evacuated from the chamber through the one or more valves to verify that the vacuum splint can hold a vacuum within the chamber.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

That which is claimed:

1. A device comprising
two layers of material, a semi-rigid member, and a plurality of discrete elements,
where the device has a head end and an opposite foot end,
where the two layers of material are fused together to form a chamber therein, where the semi-rigid member spans the length of the device from the head end to the foot end, and where the discrete elements are contained within the chamber, and where the semi-rigid member is sufficiently flexible to allow the device to be rolled.

2. The device of claim 1, wherein the device further comprises two protrusions, where these two protrusions are located at the head end of the device, where there is one protrusion on either side of the device, where each protrusion extends in a direction away from the foot end.

3. The device of claim 2, wherein the protrusions are formed from the two layers of material.

4. The device of claim 1, further comprising a valve, which provides access to the chamber for removal of air contained therein or introduction of air thereto.

5. The device of claim 1, wherein the semi-rigid member resists compressive forces along a longitudinal axis of the semi-rigid member.

6. The device of claim 1, further comprising an additional layer of material; where the additional layer of material is fused to one of the two layers of material forming a sleeve therein, and where the semi-rigid member resides within the sleeve.

7. The device of claim 1, wherein the semi-rigid member comprises polyethylene.

8. The device of claim 1, further comprising a rigid support, where the rigid support is secured to an end of the semi-rigid member.

9. A vacuum splint comprising
two layers of material, a semi-rigid member, a valve, and a plurality of beads, where the two layers of material are fused together to form a chamber therein, where the beads are contained within the chamber,
where the vacuum splint has a substantially trapezoidal shape with a head end and an opposite foot end, where the head end of the vacuum splint includes two protrusions,
where the semi-rigid member spans a length of the vacuum splint from the head end to the foot end, where the semi-rigid member resists compressive forces along a longitudinal axis of the semi-rigid member, where the semi-rigid member is flexible about a lateral axis such that the vacuum splint may be rolled, and
where the valve provides fluid access to the chamber.

10. The vacuum splint of claim 9, wherein the semi-rigid member comprises polyethylene.

11. The vacuum splint of claim 9, further comprising an additional layer of material, where the additional layer of material is fused to one of the two layers of material forming a sleeve therein, and where the semi-rigid member resides within the sleeve.

12. The vacuum splint of claim 9, wherein each bead comprises polystyrene.

13. The vacuum splint of claim 9, further comprising an additional valve, where the valve and the additional valve are located at opposite ends of the vacuum splint.

14. The vacuum splint of claim 9, further comprising a rigid support, where the rigid support is secured to an end of the semi-rigid member.

15. A method of transporting a patient comprising the steps of
obtaining a vacuum splint, where the vacuum splint comprises two layers of material, a semi-rigid member, a valve, and a plurality of beads, where the two layers of material are fused together to form a chamber therein, where the semi-rigid member spans a length of the vacuum splint from a head end to an opposite foot end, where the semi-rigid member is sufficiently flexible about a lateral axis to be rolled, where the beads are contained within the chamber, and where the valve provides fluid access to the chamber
placing the patient upon the vacuum splint,
forming the vacuum splint around the patient and
evacuating air from within the chamber through the valve thereby causing the vacuum splint to stiffen.

16. The method of claim 15, wherein the vacuum splint further comprises two protrusions, where these two protrusions are located at the head end of the vacuum splint, where there is one protrusion on either side of the device.

17. The method of claim 16, wherein the protrusions are formed from the two layers of material.

18. The method of claim 16, wherein the step of forming the vacuum splint around the patient includes forming the two protrusions around a head of a patient.

19. The method of claim 15, further comprising the step of opening the valve whereby air is allowed to enter the chamber thereby causing the vacuum splint to soften.

20. The method of claim 15, wherein the vacuum splint further comprises a rigid support, where the rigid support is secured to an end of the semi-rigid member, wherein the semi-rigid member resists compressive forces along a longitudinal axis of the semi-rigid member.

* * * * *